United States Patent [19]

Porath

[11] Patent Number: 4,897,467

[45] Date of Patent: Jan. 30, 1990

[54] NITRILOPHORIC EDA-ADSORBENTS

[75] Inventor: Jerker O. Porath, Upsala, Sweden

[73] Assignee: Gelinnovation H.B., Lidingo, Sweden

[21] Appl. No.: 12,658

[22] Filed: Feb. 9, 1987

[30] Foreign Application Priority Data

Feb. 13, 1986 [SE] Sweden ................................ 8600641

[51] Int. Cl.$^4$ ...................... C08L 89/00; C08L 89/02; C08L 89/04; B01J 20/00

[52] U.S. Cl. .................................... 530/415; 525/54.1; 502/402; 502/404; 502/405; 210/656; 210/660; 210/927

[58] Field of Search .................. 127/55; 502/400, 401, 502/402, 403, 404, 405, 407, 439; 252/184; 525/54.1; 210/656, 927, 660; 530/334, 415

[56] References Cited

U.S. PATENT DOCUMENTS 3,705,084 12/1972 Reynolds ............................ 435/180
4,597,999 7/1986 Lingwood ............................ 424/88

FOREIGN PATENT DOCUMENTS 1902226 7/1970 Fed. Rep. of Germany.
1592702 7/1981 United Kingdom.

*Primary Examiner*—John Kight
*Assistant Examiner*—Nathan M. Nutter
*Attorney, Agent, or Firm*—Young & Thompson

[57] ABSTRACT

An adsorbent that comprises a solid phase for the isolation and immobilization of proteins by adsorption from a liquid phase is characterized in that it consists of a hydrophilic polymer network with covalently bound ligands of the formula

—Y—X—R, in which R is an aliphatic substituent containing at least one nitrile group or a substituent having a heterocyclic ring system with at least one nitrogen atom in the ring and with one or more side groups consisting of or including —CN (nitrile group), where X is NQ, S, or O, Q being $H(CH_2)_n$, where $n=0, 1, 2$ or 3, and Y is a side chain which joins R-X with the polymer network.

The polymer preferably consists of agar or agarose in particle form having a particle size of <1 mm. Y can be —$CH_2$—$CH_2SO_2$—$CH_2$—$CH_2$— and R can be

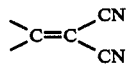

The adsorbent can be used to isolate biopolymers and, inter alia, has been found highly effective in isolating proteins. The adsorbent can be produced by first activating the polymer with divinylsulphone and then adding the ligands.

14 Claims, 1 Drawing Sheet

NITRILOPHORIC EDA-ADSORBENTS

The present invention relates to nitrilophoric adsorbents of the kind which incorporate a solid phase for the isolation and immobilization of proteins by adsorption from a solid phase.

Biochemical separating processes for isolating on a laboratory scale proteins and other substances which are present in extremely low concentrations, or are present together with lipids and other not-readily separated substances, or which are membrane-bound, are difficult to perform and require the application of effective methods. Rapid, highly selective biotechnological downstream processes also require new adsorbents if high yields are to be obtained.

Chromatography is mainly directed to so-called H.P.L.C. and F.P.L.C. which have an effect that is unsuitable for industrial applications. For industrial applications, one can be expected to require biotechnological downstream processes which are effected N-dimensionally with rapid adsorption-desorption processes. The separation of substances can be achieved in a multiplicity of "dimensions" by basing these processes on group selective methods which will provide sharply defined classifications, and also on the use of group-selective adsorbents. We have earlier developed three different kinds of salting-out adsorbents, namely hydrophobic or amphilic adsorbents for hydrophobic interaction chromatography, IMA-adsorbents (metal-ketal-gels), and "thiophilic" adsorbents (T-gels). The present invention relates to a novel type of adsorbent, nitrilophoric EDA-adsorbents.

The adsorbent according to the invention is characterized in that it comprises a hydrophilic network with covalently bound ligands, of the structure

—Y—X—R where R is an aliphatic substituent having at least one nitrile group or a substituent having a heterocyclic ring system with at least one nitrogen atom in the ring and with one or more side groups consisting of or comprising —CN, X is NQ, S or O, where Q is $H(CH_2)_n$, in which n=0, 1, 2 or 3, and Y is a side chain which connects R-X with the polymer network.

Among the gels produced by us are, for instance

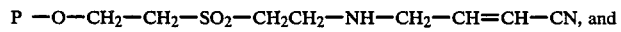

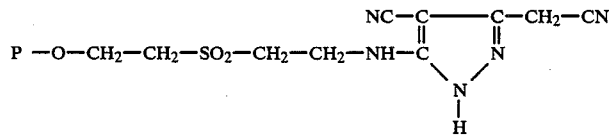

in which P is the polymer network.

The simplest of the ligands that we have studied has the structure

When this ligand is coupled to agarose by the divinylsulphone method, there is obtained an adsorbent which in all essential respects resembles our earlier thiophilic gels, i.e. an adsorbent which will adsorb immuglobulins selectively from human wholeserum. This is both unexpected and surprising. Preliminary studies indicate that the characteristic properties are dependent on the —$SO_2$-group, as with the T-gel.

The number of proteins adsorbed increases with an increasing number of cyan groups in the ligands. This becomes more manifest when the cyan groups are bound to a carbon atom that is joined to another carbon atom over a double bond, since substances that have this structure are known to possess semiconductor properties. Tetracyanethylene and tetracyandimethane benzoquinone, for instance, are organic semiconductors that have long been known to the art. This is therefore of particular interest. Such compounds owe their electrotechnical properties to their ability to accept electrons from a suitable donor system.

A number of gels that incorporate unsaturated nitrilophoric ligands have been prepared and examined, and the most interesting of these have the ligand structure

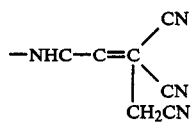

The properties of this gel are completely different to those of thio-aromatic gels, and the gel selects totally different proteins from a serum that passes through a T-gel bed.

The unsaturated nitrilophoric ligands constitute electron acceptors and adsorption is achieved as a result of the coupling established between these acceptors and electron donors located on the surfaces of the protein molecules, i.e. EDA-adsorption (Electron-Donor-Acceptor).

Synthesis of nitrilophoric adsorbents will be described hereinafter in more detail with reference to a number of working examples.

EXAMPLE 1

A. In the preparation of a divinylsulphone-activated polymer network, 100 g of particulate agarose swollen in 100 ml of 0.1M sodium carbonate, pH 12, were admixed with 100 ml of the same carbonate buffer and 10 ml of divinylsulphone. The resultant suspension was allowed to stand for 15 hours while being gently stirred. The gel particles were separated from the suspension and washed, first with distilled water and then with a 0.1M sodium carbonate buffer, pH 10, and used immediately in the manufacture of an adsorbent.

B. The dinvinylsulphone-activated gel according to A was slurried in 100 ml of a 0.1M sodium carbonate buffer, pH 10, and 10 g of aminoacetonitrile were added to the slurry, which was then stirred for 20 hours. The gel was filtered off on a suction filter, and then washed with water and also with the buffer that was subsequently used in the adsorption process. The gel contained about 500 micromoles of ligand for each gram of dry gel substance produced.

EXAMPLE 2

The procedure followed in this example was the same as that recited in Example 1, but with the difference that agarose was replaced with hydroxy-propylated silicagel and that the sodium carbonate buffer was replaced with an NaHCO$_3$-buffer of pH 9.5. In part A of the process the suspension was left to stand for 5 hours and in part B for 10 hours, as opposed to 15 hours and 20 hours, respectively, in parts A and B of the process described in Example 1. The gel contained 50 micromoles of ligand for each gram of dry gel produced.

EXAMPLE 3

The procedure here was the same as that for Example 1, but with 3-aminocrotonnitrile instead of aminoacetonitrile. The gel contained about 300 micromoles of ligand for each gram of dry gel produced.

EXAMPLE 4

The procedure here was the same as with Example 1, but with 2-amino-1,1,3-tricyanopropylene instead of aminoacetonitrile. The gel contained about 500 micromoles of ligand for each gram of dry gel produced.

EXAMPLE 5

The process carried out in this Example was the same as that carried out in Example 1, but with the use of 5-amino-4-cyano-3-cyanomethyl-pyrazol instead of aminoacetonitrile. The gel contained about 200 micromoles of ligand for each gram of dry gel produced.

EXAMPLE 6

Approximately 10 g of a porous cellulose product comprising mutually braided fibres ("wettex" cloth or paper) were activated with divinylsulphone, by immersing the fibres in a solution of 5% divinylsulphone in a 0.1M sodium carbonate solution. The cellulose cloths were removed from the solution bath after 10 hours and washed first with water and then with 0.1M NaHCO$_3$, which was adjusted to pH 10 with NaOH. The cloths were then placed in a bath that contained 0.1 g of 2-amino-1,1,3-tricyanopropylene in 30 ml of 0.1M sodium carbonate solution, pH 10. The cloths were removed from the bath after 20 hours and washed first with water and then with the buffer that was subsequently used for testing the adsorption properties of the cloth.

When testing the adsorbent properties of the cloth, the cloth was laid around the inner wall surfaces of a glass beaker into which a test solution (intestinal villi extract in 0.5M K$_2$SO$_4$, tris-buffer, pH 7.6) was poured, so as to cover the cloth. The solution was stirred with a magnetic stirrer for one hour, during which period the phosphatase activity was adsorbed on the cloth. The enzyme was washed out with distilled water. When a comparison test was run with a cellulose cloth to which ethanolamine had been coupled instead of 2-amino-1,1,3-tricyanopropylene, no phosphatase from the intestinal villi extract was adsorbed on the cloth.

Fractionation of serum protein

Salting-out chromatography was applied on an adsorbent that contained a nitrile group. A tandem column was coupled in series to four 10 ml beds containing divinylsulphone cross-linked with agarose (6%) substituted with (1) aminoacetonitrile (AN), (2) 3-aminocrotonnitrile (CN), (3) 2-amino-1,1,3-cyanopropylene (TCP) and 5-amino-4-cyano-3-cyanomethylpyrazol (CPY). The tandem beds were brought into equilibrium by washing the same with a 0.05M tris-buffer (tris-hydroxymethylaminomethane) containing 0.5M K$_2$SO$_4$.

10 ml of serum dialyzed against the equilibrium buffer were charged to the beds, followed by 50 ml of equilibrium buffer. The passing material was taken up in two fractions (E$_1$ and E$_2$). The tandem beds were taken apart and each bed was eluted per se, by washing the same with a tris-buffer that contained no K$_2$SO$_4$.

Figure 1B:
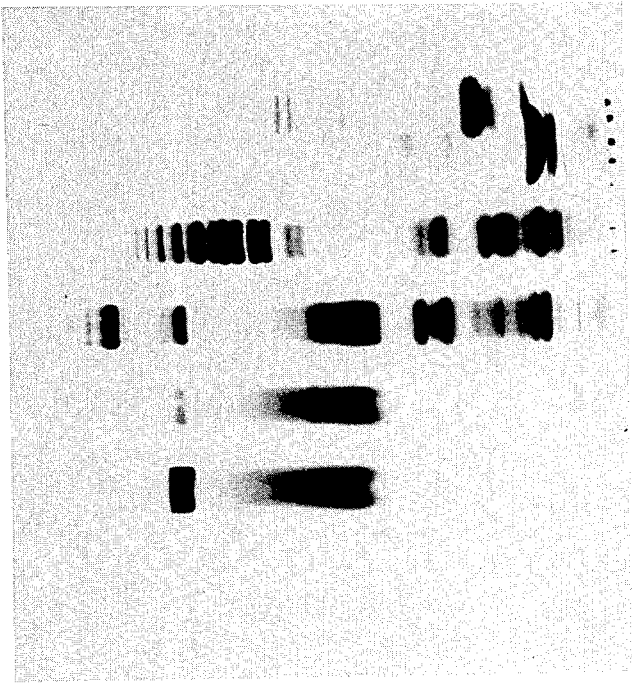
FIGS. 1$a$ and 1$b$ illustrate respectively an agarose-gel electrophoresis and a polyacryl-gel-gradient-electrophoresis diagram of fractions eluted from the separated beds and the two eluted fractions E$_1$ and E$_2$ from the composite column.
Figure 1A:

The diagram shows that good group classification of the serum proteins was obtained. Most protein was adsorbed on the AN-gel (15–20%) and the next largest proportion of protein was adsorbed on the TCP-gel (5–10%), whereas 45–50% of the protein passed through the tandem column, the major part consisting of serum albumin.

Immunoprecipitation according to Ouchterlony showed that the various fractions had the following protein content:

AN: IgG, IgA, $\alpha_{2M}$
CN: IgG, IgA,
TCP: IgG, IgA, C$_3$, C$_4$, ceruloplasmin, $\alpha_{2M}$
CPY: haptoglobin, ceruloplasmin, transferrin, hemopexin,
E$_1$: albumin, $\alpha_1$-antitrypsin, orosomukoid, prealbumin, and
E$_2$: transferrin.

This shows that the nitrilophoric gels supplement other salting-out adsorbents and should therefore be incorporated in the gels on which protein fractionation is based. Preliminary tests have already shown this to be the case, and that when the immunoglobulins are isolated from the starting material, a still more sharply defined group fractionation is achieved.

Fractionation of intestinal villi extract (villi intestinalis)

25 ml of an intestinal villi extract containing 150 mg of solids and dissolved in 0.5M K$_2$SO$_4$, 0.05M tris-HCL, pH 7.6, were introduced into a tandem column of the same kind as that used in the serum protein example. The following protein distribution (measured by adsorption at 280 nm) and phosphatase activity was obtained subsequent to washing, separating and eluting the separate beds.

|  |  | adsorbence 280 nm | activity |
|---|---|---|---|
| AN | I | 0.8 | 0.002 |
|  | II | 1.0 | 0.011 |
| CN | I | 0.2 | — |
|  | II | 0.6 | 0.002 |
| TCP | I | 2.0 | 0.385 |
|  | II | 1.2 | 0.028 |
| CPY | I | 1.3 | 1.32 |
|  | II | 0.4 | — |
| passed |  | 102 | 0.008 |

Thus the alkaline phosphatase is enriched from 30 to 40 times in a single stage. This phosphatase has wide use in ELISA-tests and is particularly expensive.

Comparison between nitrilophoric gels, T-gels and thio-aromatic adsorbents

The nitrilophoric and thio-aromatic adsorbents both have a feature in common with the T-gel, insomuch that they all adsorb immunoglobulins. The simplest nitrilophoric gel and the T-gel are remarkably similar with respect to their adsorption properties. Whereas the thio-aromatic gels have a hydrophobic character, this is not at all the case with either the T-gels or the nitrilophoric gels. Gels which possess a multiplicity of nitrile groups and vicinal double bonds are of particular interest and present an unexpected specificity. Consequently, the nitrilophoric gels introduce a new separation dimension to protein chromatography.

Because the ligands of the nitrilophoric gels will accept electrons, nucleotides, nucleic acids and other nucleophilic substances will also be adsorbed. The gels will also adsorb aromatic substances, even when present in organic or hydroorganic solvents. Consequently, nitrilophoric gels can be developed into universal adsorbents for aromatic and heteroaromatic substances.

I claim:

1. A solid adsorbent for use in the isolation and immobilization of proteins by adsorption from a liquid phase, said solid adsorbent comprised of a hydrophilic polymer network having covalently bound ligands of the formula

—Y—X—R in which R is an aliphatic substituent containing at least one nitrile group or a substituent having a heterocyclic ring system with at least one nitrogen atom in the ring with one or more side groups consisting of or including —CN, where
X is NQ, S or O,
Q is $H(CH_2)_n$ where n=0–3, and
Y is $-CH_2-CH_2-SO_2-CH_2\text{13 }CH_2-$
which joins R-X with the polymer network.

2. An adsorbent according to claim 1, characterized in that R contains the group $$>C=C<^{CN}_{CN}$$

3. An adsorbent according to claim 1, characterized in that it comprises particles <1 mm.
4. An adsorbent according to claim 1, characterized in that the polymer network comprises a polyhydroxy polymer.
5. An adsorbent according to claim 4, characterized in that the polyhydroxy polymer is a polygalactan, such as agar or agarose.
6. An adsorbent according to claim 1, characterized in that the polymer network comprises hydroxypropylated silica gel.
7. An adsorbent according to claim 1 wherein said ligand has the formula $-CH_2-CH_2-SO_2-CH_2-CH_2-NH-CH_2-CH=CH-CN$.

8. An adsorbent according to claim 1 wherein said ligand has the formula $$-CH_2-CH_2-SO_2-CH_2-CH_2-NH-C\underset{NH}{\overset{NC-C=C-CH_2-CN}{|\quad\quad\quad |}}N$$

9. A method for the production of a solid adsorbent for use in the isolation and immobilization of proteins by adsorption from a liquid phase, said solid adsorbent comprised of a hydrophilic polymer network having covalently bound ligands of the formula

—Y—X—R in which R is an aliphatic substituent containing at least one nitrile group or a substituent having a heterocyclic ring system with at least one nitrogen atom in the ring with one or more side groups consisting of or including —CN, where
X is NQ, S or O,
Q is $H(CH_2)_n$ where n=0–3, and
Y is $-CH_2-CH_2-SO_2-CH_2-CH_2-$
which joins R-X with the polymer network, said method comprising the steps of activating said polymer network by contacting same with divinylsulphone and subsequently incorporating nitrile groups onto said adsorbent.

10. A method according to claim 10 wherein said ligand has the formula $-CH_2-CH_2-SO_2-CH_2-CH_2-NH-CH_2-CH=CH-CN$.

11. A method according to claim 10 wherein said ligand has the formula $$-CH_2-CH_2-SO_2-CH_2-CH_2-NH-C\underset{NH}{\overset{NC-C=C-CH_2-CN}{|\quad\quad\quad |}}N$$

12. A method for isolating and immobilizing proteins by adsorption from a liquid phase, said method comprising contacting said proteins with a solid adsorbent comprised of a hydrophilic polymer network having covalently bound ligands of the formula

—Y—X—R in which R is an aliphatic substituent containing at least one nitrile group or a substituent having a heterocyclic ring system with at least one nitrogen atom in the ring with one or more side groups consisting of or including —CN, where
X is NQ, S or O,
Q is $H(CH_2)_n$ where n=0–3, and
Y is $-CH_2-CH_2-SO_2-CH_2-CH_2-$
which joins R-X with the polymer network.

13. A method according to claim 14 wherein said ligand has the formula $-CH_2-CH_2-SO_2-CH_2-CH_2-NH-CH_2-CH=CH-CN$.

14. A method according to claim 14 wherein said ligand has the formula $$-CH_2-CH_2-SO_2-CH_2-CH_2-NH-C\underset{NH}{\overset{NC-C=C-CH_2-CN}{|\quad\quad\quad |}}N$$

* * * * *